(12) United States Patent
Zhang

(10) Patent No.: US 7,847,041 B2
(45) Date of Patent: Dec. 7, 2010

(54) COBALT-CATALYZED ASYMMETRIC CYCLOPROPANATION OF ELECTRON-DEFICIENT OLEFINS

(75) Inventor: X. Peter Zhang, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 12/205,373

(22) Filed: Sep. 5, 2008

(65) Prior Publication Data

US 2009/0069519 A1   Mar. 12, 2009

Related U.S. Application Data

(60) Provisional application No. 60/970,691, filed on Sep. 7, 2007.

(51) Int. Cl.
*C08F 4/00* (2006.01)
*C08F 4/04* (2006.01)

(52) U.S. Cl. .......................... 526/172; 526/93

(58) Field of Classification Search .................. 526/172
See application file for complete search history.

(56) References Cited

U.S. PATENT DOCUMENTS

2006/0030718 A1   2/2006   Zhang et al.

OTHER PUBLICATIONS

U.S. Appl. No. 12/404,435, Zhang et al.*
U.S. Appl. No. 11/215,347, Zhang et al.*
Artaud et al., C.R. Acad. Sc. Paris 1976, 503-505,283.
Ashton et al, J. Med. Chem. 1988, 2304-2315, 31 (12).
Bonavent et al., Bull. Soc. Chim. Fr. 1964, 2462-2471, 398.
Caselli et al., Inorganica Chimica Acta 2006, 2924-2932, 359.
Cativiela et al., Tetrahedron: Asymmetry 2000, 645-732, 11.
Charette et al., Adv. Synth. Catal. 2005, 1547-1552, 347.
Che et al., J. Am. Chem. Soc. 2001, 4119-4129, 123 (18).
Chen et al., J. Am. Chem. Soc. 2004, 14718-14719, 126 (45).
Chen et al., Tetrahedron 2005, 4965-4969, 46.
Chen et al., J. Org. Chem. 2007, 5931-5934, 72 (15).
Csuk et al., Tetrahedron 1994, 1043-10442, 50 (35).
Danishefsky, Acc. Chem. Res. 1979, 66-72, 12 (2).
Davies et al., J. Am. Chem. Soc. 1996, 6897-6907, 118 (29).
Denmark et al., J. Org. Chem. 1997, 3375-3389, 62 (10).
Donaldson, Tetrahedron 2001, 8589-8627, 57.
Doyle et al., J. Org. Chem. 1980, 1538-1539, 45 (8).
Doyle et al., J. Org. Chem. 1982, 4059-4068, 47 (21).
Doyle et al., J. Am. Chem. Soc. 1993, 9968-9978, 115 (22).
Doyle et al., Chem. Rev. 1998, 911-936, 98 (2).
Evans et al., J. Am. Chem. Soc. 1991, 726-728, 113 (2).
Fritschi et al., Angew. Chem. Int. Ed. Engl. 1986, 1005-1006, 25 (11).
Gnad et al., Chem. Rev. 2003, 1603-1624, 103 (4).
Hammerschmidt et al., Liebigs Ann. Chem. 1977, 1026-1038.
Huang et al., J. Org. Chem. 2003, 8179-8184, 68 (21).
Jeromin et al., Ger. Offen. 2006.
Jonczyk et al., Communications 1976, 387-388.
Kennewell et al., J. Chem. Soc. Perkin Trans. 1 1982, 2563-2570.
Kozhushkov et al., Synthesis 2003, 956-958, 5 (6).
Lebel et al., Chem. Rev. 2003, 977-1050, 103 (4).
Lo et al., J. Am. Chem. Soc. 1998, 10270-10271, 120 (39).
Maxwell et al., Organometallics 1992, 645-652, 11 (2).
Miller et al., Angew. Chem. Int. Ed. 2002, 2953-2956, 41 (16).
Miller et al., Angew. Chem. Int. Ed. 2005, 3885-3889, 44.
Nakamura et al., J. Am. Chem. Soc. 1978, 3443-3448, 100 (11).
Nishiyama et al., J. Am. Chem. Soc. 1994, 2223-2224, 116 (5).
Ornstein et al., J. Med. Chem. 1998, 346-357, 41 (3).
Padwa et al., Tetrahedron 1992, 5385-5453, 48 (26).
Papageorgiou et al., Angew. Chem. Int. Ed. 2003, 828-831, 42 (7).
Penoni et al., Eur. J. Inorg. Chem. 2003, 1452-1460.
Pietruszka J., Chem. Rev. 2003, 1051-1070, 103 (4).
Salaun J., Chem. Rev. 1989, 1247-1270, 89 (5).
Son et al., J. Am. Chem. Soc. 2007, 1046-1047, 129 (5).
Wessjohann et al., Chem. Rev. 2003, 1625-1648, 103 (4).
Wong et al., Chem. Rev. 1989, 165-198, 89 (1).
Davies et al., "Intermolecular Metal-Catalyzed Carbenoid Cyclopropanations." Organic Reactions, 2001, 1-326, John Wiley & Sons, New York.
Gao et al., "Catalytic asymmetric cyclopropanation at a chiral platform." Org. Biomol. Chem. 2005, 2126-2128, vol. 3.

* cited by examiner

*Primary Examiner* — Ling-Siu Choi
*Assistant Examiner* — Sonya Wright
(74) *Attorney, Agent, or Firm* — Bryan Cave LLP

(57) ABSTRACT

Cobalt-catalyzed asymmetric cyclopropanation of electron-deficient olefins.

49 Claims, No Drawings

COBALT-CATALYZED ASYMMETRIC CYCLOPROPANATION OF ELECTRON-DEFICIENT OLEFINS

CROSS-REFERENCE TO RELATED APPLICATIONS

This application claims priority to U.S. Provisional Application Ser. No. 60/970,691, filed Sep. 7, 2007, which is incorporated herein by reference in its entirety.

STATEMENT OF GOVERNMENT RIGHTS

This invention was made with Government support under grant number NSF 0711024 awarded by the National Science Foundation and grant number 44286-AC1 awarded by the American Chemical Society. The government has certain rights in the invention.

FIELD OF THE INVENTION

The present invention generally relates to metal-catalyzed cyclopropanation of olefins. More particularly, the present invention relates to a process for asymmetric cyclopropanation of electron-deficient olefins using a cobalt porphyrin complex.

BACKGROUND OF THE INVENTION

Metal-catalyzed cyclopropanation of olefins with diazo reagents has attracted great research interest because of its fundamental and practical importance. (Lebel et al., Chem. Rev. 2003, 103, 977; Davies H. M. L., Antoulinakis E., Org. React. 2001, 57, 1; Doyle M. P., Forbes D. C., Chem. Rev. 1998, 98, 911; and Padwa A., Krumpe K. E., Tetrahedron 1992, 48, 5385-5453.) The resulting cyclopropyl units are recurrent motifs in biologically important molecules and serve as versatile precursors in organic synthesis. (Pietruszka J., Chem. Rev. 2003, 103, 1051; Wessjohann et al., Chem. Rev. 2003, 103, 1625; Donaldson W. A., Tetrahedron 2001, 57, 8589; and Salaun J., Chem. Rev. 1989, 89, 1247.) In the past two decades, outstanding asymmetric catalytic processes, notably those based on copper, rhodium and ruthenium have been developed to allow for the synthesis of chiral cyclopropane derivatives from olefins with diazoacetates in high yields and high selectivities. (Fritschi et al., Agnew. Chem., Int. Ed. Engl. 1986, 25, 1005; Evans et al., J. Am. Chem. Soc. 1991, 113, 726; Lo et al., J. Am. Chem. Soc. 1998, 120, 10270; Maxwell et al., Organometallics 1992, 11, 645; Doyle et al., J. Am. Chem. Soc. 1993, 115, 9968; Davies et al., J. Am. Chem. Soc. 1996, 118, 6897; Nishiyama et al., J. Am. Chem. Soc. 1994, 116, 2223; and Che et al., J. Am. Chem. Soc. 2001, 123, 4119.)

While a number of catalytic systems worked exceptionally well with styrene derivatives and some electron-rich olefins, asymmetric cyclopropanation of electron-deficient olefins containing electron-withdrawing groups such as α,β-unsaturated carbonyl compounds and nitriles have proven to be a challenging problem presumably due to the electrophilic nature of the metal-carbene intermediates in the catalytic cycles. This catalytic asymmetric process would be highly desirable as the corresponding electrophilic cyclopropanes containing two or more electron-withdrawing groups have shown to be valuable synthetic intermediates for various applications. (Gnad F., Reiser O., Chem. Rev. 2003, 103, 1603; Cativiela C., Diaz-de-Villegas, M. D., Tetrahedron: Asy. 2000, 11, 645; Wong et al., Chem. Rev. 1989, 89, 165; and Danishefsky, Acc. Chem. Res. 1979, 12, 66.)

Among several previous efforts towards metal-catalyzed cyclopropanation of electron-deficient olefins with diazo reagents (Doyle et al., J. Org. Chem. 1980, 45, 1538; Doyle et al., J. Org. Chem. 1982, 47, 4059; Nakamura et al., J. Am. Chem. Soc. 1978, 100, 3443; Denmark et al., J. Org. Chem. 1997, 62, 3375), the most notable example is the (Salen)Ru-based asymmetric catalytic system recently reported by Nguyen and coworkers (Miller et al., Angew. Chem., Int. Ed. 2002, 41, 2953; and Miller et al., Angew. Chem., Int. Ed. 2005, 44, 3885). (For intramolecular asymmetric cyclopropanation of electron-deficient olefins, see: Lin W., Charette A. B., Adv. Synth. Catal. 2005, 347, 1547; for a Cu-catalyzed asymmetric [4+1] cycloaddition of α,β-unsaturated ketones with diazoacetates, see: Son S., Fu G. C., J. Am. Chem. Soc. 2007, 129, 1046; for an organocatalytic process, see: Papageorgiou et al., Agnew. Chem., Int. Ed. Engl. 2003, 42, 828.)

It was shown that methyl methacrylate could be effectively cyclopropanated with ethyl diazoacetate (EDA) using a 5:1 ratio of olefin:EDA, producing the desired product in high yield and high selectivities (both diastereoselectivity and enantioselectivity). However, only moderate results were obtained with acrylonitrile even when the reactions were run in neat olefin.

SUMMARY OF THE INVENTION

The present invention provides for a general and efficient catalytic system for asymmetric cyclopropanation of electron-deficient olefins. The cobalt (II) complex of the $D_2$-symmetric chiral porphyrin can cyclopropanate a wide range of electron-deficient olefins, forming the corresponding electrophilic cyclopropane derivatives in high yields and selectivities.

Among the various aspects of the present invention is a process for the asymmetric cyclopropanation of electron-deficient olefins with a cobalt(II) complex of a $D_2$-symmetric chiral porphyrin [Co(1)].

The present invention is further directed to a process for asymmetric cyclopropanation of an olefin wherein at least one of the olefinic carbon atoms possesses an electron withdrawing group. The process comprises treating the olefin with a diazo ester in the presence of a chiral porphyrin complex.

Other objects and features will be in part apparent and in part pointed out hereinafter.

ABBREVIATIONS AND DEFINITIONS

The following definitions and methods are provided to better define the present invention and to guide those of ordinary skill in the art in the practice of the present invention. Unless otherwise noted, terms are to be understood according to conventional usage by those of ordinary skill in the relevant art.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl, and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substitutents include halogen, heterocyclo, alkoxy, alkenoxy, alkynoxy, aryloxy, hydroxyl, protected hydroxy, keto, acyl, acyloxy, nitro, amino, amido, nitro, cyano, thiol, ketals, acetals, esters and ethers.

The term "heteroatom" shall mean atoms other than carbon and hydrogen.

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl, and the like. The substituted alkyl groups described herein may have, as substituents, any of the substituents identified as substituted hydrocarbyl substituents.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term alkoxy or alkoxyl shall mean any univalent radical, RO⁻ where R is an alkyl group.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl. The substituted aryl groups described herein may have, as substituents, any of the substituents identified as substituted hydrocarbyl substituents.

The terms "halogen" or "halo" as used herein alone or as part of another group refer to chlorine, bromine, fluorine, and iodine.

The terms "diazo" or "azo" as used herein describe an organic compound with two linked nitrogen compounds. These moieties include without limitation diazomethane, ethyl diazoacetate, and t-butyl diazoacetate.

DETAILED DESCRIPTION OF THE PREFERRED EMBODIMENTS

In accordance with the process of the present invention, compounds containing an ethylenic bond, commonly known as olefins, possessing an electron-deficient substituent on at least one of the ethylenic carbons (also sometimes referred to as an olefinic carbon) are cyclopropanated with a diazo reagent in the presence of a cobalt porphyrin complex. Advantageously, the metal porphyrin catalyzed process proceeds relatively efficiently under relatively mild and neutral conditions, in a one-pot fashion, with olefins as limiting reagents and without the need for slow-addition of diazo reagents.

In general, the olefin may be any of a wide range of olefins possessing an electron-deficient substituent on one, or both of the olefinic carbons. One such preferred class of olefins is α,β-unsaturated olefins possessing an electron-withdrawing substituent on the α-olefinic carbon, the β-olefinic carbon, or both. In one embodiment, therefore, the α-olefinic carbon possesses an electron-withdrawing substituent but the β-olefinic carbon does not. In another embodiment, the α-olefinic carbon and the β-olefinic carbon each possess an electron-withdrawing substituent. When the α-olefinic carbon and the β-olefinic carbon each possess an electron-withdrawing substituent, the electron-withdrawing substituents may be in the cis-conformation or the trans-conformation; in certain embodiments, they are preferably in the cis-conformation.

In one embodiment, the olefin corresponds to Formula 1:

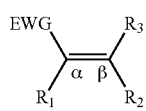

Formula 1 wherein EWG is an electron withdrawing group, $R_1$ is a substituent of the α-carbon of the ethylenic bond, and $R_2$ and $R_3$ are substituents of the β-carbon of the ethylenic bond. Preferably, $R_1$ is hydrogen, hydrocarbyl, substituted hydrocarbyl, or heterocyclo and $R_2$ and $R_3$ are independently hydrogen, hydrocarbyl, substituted hydrocarbyl, heterocyclo, or an electron withdrawing group. In one embodiment, $R_1$ is hydrogen. In another embodiment, $R_1$ is alkyl or substituted alkyl. In one embodiment, $R_2$ is hydrogen. In another embodiment, $R_2$ is alkyl or substituted alkyl. In one embodiment, $R_3$ is hydrogen. In another embodiment, $R_3$ is alkyl or substituted alkyl. In one embodiment, at least one of $R_1$, $R_2$ and $R_3$ is hydrogen and the other two are alkyl or substituted alkyl. In one embodiment, at least two of $R_1$, $R_2$ and $R_3$ are hydrogen and the other is alkyl or substituted alkyl.

When the olefin corresponds to Formula 1 and one of $R_2$ and $R_3$ is an electron withdrawing group, the olefin corresponds to Formula 1-trans or 1-cis, respectively:

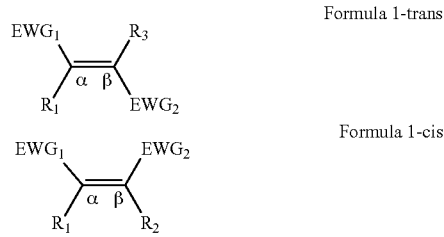

Formula 1-trans

Formula 1-cis wherein $EWG_1$ and $EWG_2$ are electron withdrawing groups and are the same or are different, $R_1$ is a substituent of the α-carbon of the ethylenic bond, and $R_2$ and $R_3$ are substituents of the β-carbon of the ethylenic bond. In this embodiment, $R_1$, $R_2$ and $R_3$ are preferably independently hydrogen, hydrocarbyl, substituted hydrocarbyl or heterocyclo.

In one preferred embodiment, the olefin corresponds to Formula 1, $R_1$ is hydrogen, and at least one of $R_2$ and $R_3$ is hydrogen. Olefins having this substitution pattern are depicted by Formula 2:

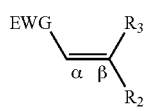

Formula 2 wherein EWG is an electron withdrawing group, and at least one of $R_2$ and $R_3$ is hydrogen. When one of $R_2$ and $R_3$ is other than hydrogen, the olefin corresponds to Formula 2-trans or Formula 2-cis:

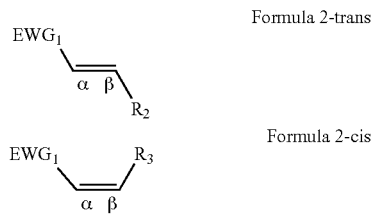

wherein $EWG_1$ is an electron withdrawing group, $R_2$ and $R_3$ are independently hydrogen, hydrocarbyl, substituted hydrocarbyl, heterocyclo, or $EWG_2$, $EWG_2$ is an electron withdrawing group, and $EWG_1$ and $EWG_2$ are the same or are different.

In another preferred embodiment, the olefin corresponds to Formula 1 and $R_1$, $R_2$ and $R_3$ are hydrogen. Olefins having this substitution pattern are depicted by Formula 3:

wherein EWG is an electron withdrawing group.

In general, the olefin's electron withdrawing group(s), for example, EWG, $EWG_1$ or $EWG_2$ as depicted in Formula 1, Formula 2, Formula 2-trans, Formula 2-cis, or Formula 3, is any substituent that draws electrons away from the ethylenic bond. Exemplary electron withdrawing groups include hydroxy, alkoxy, mercapto, halogens, carbonyls, sulfonyls, nitrile, quaternary amines, nitro, trihalomethyl, imine, amidine, oxime, thioketone, thioester, or thioamide. In one embodiment, the electron withdrawing group(s) is/are hydroxy, alkoxy, mercapto, halogen, carbonyl, sulfonyl, nitrile, quaternary amine, nitro, or trihalomethyl. In another embodiment, the electron withdrawing group(s) is/are halogen, carbonyl, nitrile, quaternary amine, nitro, or trihalomethyl. In another embodiment, the electron withdrawing group(s) is/are halogen, carbonyl, nitrile, nitro, or trihalomethyl. When the electron withdrawing group is alkoxy, it generally corresponds to the formula —OR where R is hydrocarbyl, substituted hydrocarbyl, or heterocyclo. When the electron withdrawing group is mercapto, it generally corresponds to the formula —SR where R is hydrogen, hydrocarbyl, substituted hydrocarbyl or heterocyclo. When the electron withdrawing group is a halogen atom, the electron withdrawing group may be fluoro, chloro, bromo, or iodo; typically, it will be fluoro or chloro. When the electron withdrawing group is a carbonyl, it may be an aldehyde (—C(O)H), ketone (—C(O)R), ester (—C(O)OR), acid (—C(O)OH), acid halide (—C(O)X), amide (—C(O)$NR_aR_b$), or anhydride (—C(O)OC(O)R) where R is hydrocarbyl, substituted hydrocarbyl or heterocyclo, $R_a$ and $R_b$ are independently hydrogen, hydrocarbyl, substituted hydrocarbyl or heterocyclo, and X is a halogen atom. When the electron withdrawing group is a sulfonyl, it may be an acid (—$SO_3H$) or a derivative thereof (—$SO_2R$) where R is hydrocarbyl, substituted hydrocarbyl or heterocyclo. When the electron withdrawing group is a quaternary amine, it generally corresponds to the formula —$N^+R_aR_bR_c$ where $R_a$, $R_b$ and $R_c$ are independently hydrogen, hydrocarbyl, substituted hydrocarbyl or heterocyclo. When the electron withdrawing group is a trihalomethyl, it is preferably trifluoromethyl or trichloromethyl. In each of the foregoing exemplary electron withdrawing groups containing the variable "X", in one embodiment, X may be chloro or fluoro, preferably fluoro. In each of the foregoing exemplary electron withdrawing groups containing the variable "R", R may be alkyl. In each of the foregoing exemplary electron withdrawing groups containing the variable "$R_a$" and "$R_b$", $R_a$ and $R_b$ may independently be hydrogen or alkyl.

In general, α,β-unsaturated carbonyl compounds and α,β-unsaturated nitriles are preferred olefins for cyclopropanation. In one embodiment, therefore, the olefin's electron withdrawing group(s), for example, EWG, $EWG_1$ or $EWG_2$ as depicted in Formula 1, Formula 2, Formula 2-trans, Formula 2-cis, or Formula 3, is/are a carbonyl or a nitrile. For other applications, it may nonetheless be preferred that one or both of the ethylenic carbons of the olefin possess a quaternary amine, nitro, or trihalomethyl substituent.

In accordance with one preferred embodiment, the electron withdrawing group(s) is/are a halide, aldehyde, ketone, ester, carboxylic acid, amide, acyl chloride, trifluoromethyl, nitrile, sulfonic acid, ammonia, amine, or a nitro group. In this embodiment, the electron withdrawing group(s) correspond to one of the following chemical structures: —X, —C(O)H, —C(O)R, —C(O)OR, —C(O)OH, —C(O)X, —C(X)$_3$, —CN, —$SO_3H$, —$N^+H_3$, —$N^+R_3$, or —$N^+O_2$ where R is hydrocarbyl, substituted hydrocarbyl or heterocyclo and X is halogen.

In general, the olefin is cyclopropanated with a carbene. Preferably, the carbene precursor is a diazo reagent (also sometimes referred to herein as a diazo compound) wherein the carbene is generated by the removal of $N_2$ as nitrogen gas from the solution. More preferably, the carbene precursor is a diazo carbonyl compound. Still more preferably, the carbene precursor is a diazo ester. In some embodiments, the diazo compound is selected from the group consisting of diazo ethylacetate, diazo-t-butylacetate, 2,6-di-tert-butyl-4-methylphenyl diazoacetate, methyl phenyldiazoacetate, ethyl diazoacetate, diethyl diazomalonate, and trimethylsilyldiazomethane. In some embodiments, the diazo compound is selected from one of diazo ethylacetate and diazo t-butylacetate. In one preferred embodiment, the diazo compound has the formula $N_2CHC(O)OR_{10}$ where $R_{10}$ is hydrocarbyl, substituted hydrocarbyl or heterocyclo. In one such preferred embodiment, the diazo compound has the formula $N_2CHC(O)OR_{10}$ where $R_{10}$ is alkyl, aryl or alkaryl, more lower alkyl or aryl. Other exemplary diazo acetates include 2,3,4-trimethyl-3-pentyl diazoacetate, menthyl diazoacetate, 2,5-dimethyl-4-buten-1-yl diazoacetate, 3-(diazoacetyl)amino propionate, and (diazoacetyl)amino acetate.

In accordance with one embodiment of the present invention, an olefin is converted to a cyclopropane as illustrated in Reaction Scheme A:

Reaction Scheme A

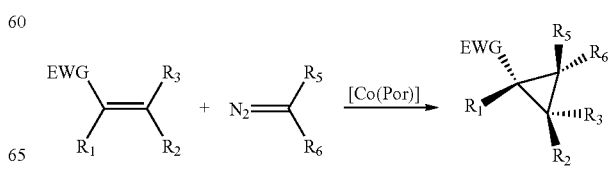

wherein [Co(Por)] is a cobalt porphyrin complex, $R_1$ is hydrogen, hydrocarbyl, substituted hydrocarbyl, or heterocyclo, $R_2$, and $R_3$ are independently hydrogen, hydrocarbyl, substituted hydrocarbyl, heterocyclo, or $EWG_2$, $R_5$ and $R_6$ are independently hydrogen, hydrocarbyl, substituted hydrocarbyl, or heterocyclo, provided one of $R_5$ and $R_6$ is carbonyl, and EWG and $EWG_2$ are independently an electron-withdrawing group. In a preferred embodiment, one of $R_5$ and $R_6$ is hydrogen and the other is carbonyl. In a more preferred embodiment, one of $R_5$ and $R_6$ is hydrogen and the other is an ester (—C(O)OR wherein R is hydrocarbyl, substituted hydrocarbyl, or heterocyclo).

In one preferred embodiment, an olefin is converted to a cyclopropane as illustrated in Reaction Scheme 1.

Reaction Scheme 1

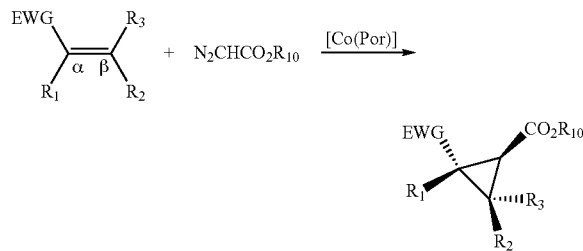

wherein [Co(Por)] is a cobalt porphyrin complex; $R_1$ is hydrogen, hydrocarbyl, substituted hydrocarbyl, or heterocyclo, $R_2$, and $R_3$ are independently hydrogen, hydrocarbyl, substituted hydrocarbyl, heterocyclo, or $EWG_2$, $R_{10}$ is hydrocarbyl, substituted hydrocarbyl, or heterocyclo, and EWG and $EWG_2$ are independently an electron-withdrawing group.

In accordance with one preferred embodiment, the electron withdrawing group, EWG, is a carbonyl or nitrile group and reaction proceeds as depicted in Reaction Schemes 2 and 3, respectively:

Reaction Scheme 2

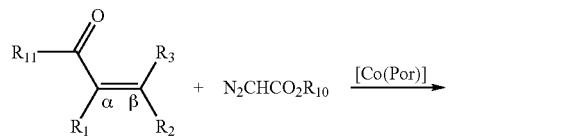

Reaction Scheme 3

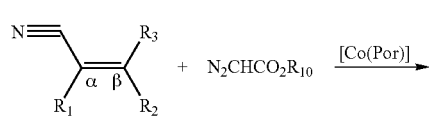

-continued

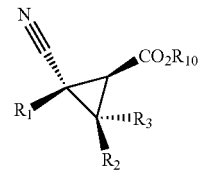

wherein [Co(Por)] is a cobalt porphyrin complex, $R_1$ is hydrogen, hydrocarbyl, substituted hydrocarbyl, or heterocyclo, $R_2$, and $R_3$ are independently hydrogen, hydrocarbyl, substituted hydrocarbyl, heterocyclo, or $EWG_2$, $R_{10}$ is hydrocarbyl, substituted hydrocarbyl, or heterocyclo, $R_{11}$ is hydrogen, hydrocarbyl, substituted hydrocarbyl, heterocyclo, —$NR_aR_b$, —$OR_a$, or —$OC(O)OC(O)R_a$, $R_a$ and $R_b$ are independently hydrogen, hydrocarbyl, substituted hydrocarbyl or heterocyclo, and EWG and $EWG_2$ are independently an electron-withdrawing group. In one such embodiment in which the cyclopropanation reaction proceeds as set forth as depicted in Reaction Scheme 2 or 3, $R_1$ is hydrogen. In another embodiment in which the cyclopropanation reaction proceeds as depicted in Reaction Scheme 2 or 3, $R_1$ is hydrogen and $R_2$ and $R_3$ are independently hydrogen, hydrocarbyl, substituted hydrocarbyl or heterocyclo. In another embodiment in which the cyclopropanation reaction proceeds as depicted in Reaction Scheme 2 or 3, $R_1$ is hydrogen and one of $R_2$ and $R_3$ is hydrogen. In another embodiment in which the cyclopropanation reaction proceeds as depicted in Reaction Scheme 2 or 3, $R_1$ is hydrogen, one of $R_2$ and $R_3$ is hydrogen, and the other of $R_2$ and $R_3$ is hydrocarbyl, substituted hydrocarbyl, or heterocyclo. In a further embodiment, $R_{10}$ may be alkyl, typically lower alkyl.

In accordance with one embodiment, each of the ethylenic carbons possesses an electron withdrawing group and the cyclopropanation reaction proceeds as depicted in Reaction Scheme 4 or 5:

Reaction Scheme 4

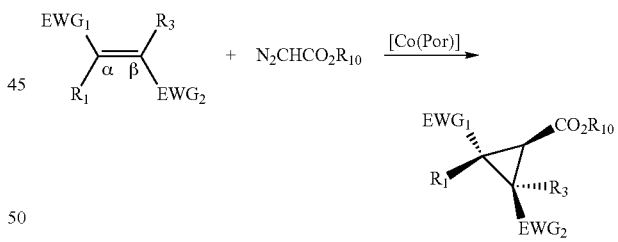

Reaction Scheme 5

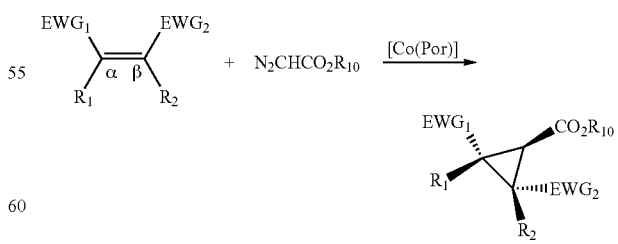

wherein [Co(Por)] is a cobalt porphyrin complex, $R_1$, $R_2$, and $R_3$ are independently hydrogen, hydrocarbyl, substituted hydrocarbyl, heterocyclo, $R_{10}$ is hydrocarbyl, substituted hydrocarbyl, or heterocyclo, and $EWG_1$ and $EWG_2$ are independently an electron-withdrawing group. In one such embodiment in which the cyclopropanation reaction proceeds as set forth as depicted in Reaction Scheme 4 or 5, $R_1$ is hydrogen. In another embodiment in which the cyclopropanation reaction proceeds as set forth as depicted in Reaction Scheme 4 or 5, $R_1$ is hydrogen and $R_2$ and $R_3$ are hydrogen, hydrocarbyl, substituted hydrocarbyl or heterocyclo. In another embodiment in which the cyclopropanation reaction proceeds as depicted in Reaction Scheme 4 or 5, $R_1$ is hydrogen and $R_2$ or $R_3$ is hydrogen. In another embodiment in which the cyclopropanation reaction proceeds as depicted in Reaction Scheme 4 or 5, $R_1$ is hydrogen, and $R_2$ or $R_3$ is hydrocarbyl, substituted hydrocarbyl, or heterocyclo. In a further embodiment, $R_{10}$ may be alkyl, typically lower alkyl.

The enantioselectivity and diastereoselectivity can be influenced, at least in part, by selection of the cobalt porphyrin complex. Similarly, stereoselectivity of the reaction may also be influenced by the selection of chiral porphyrin ligands with desired electronic, steric, and chiral environments. Accordingly, the catalytic system of the present invention may advantageously be used to control stereoselectivity.

The porphyrin with which cobalt is complexed may be any of a wide range of porphyrins known in the art. Exemplary porphyrins are described in U.S. Patent Publication Nos. 2005/0124596 and 2006/0030718 and U.S. Pat. No. 6,951, 934 (each of which is incorporated herein by reference, in its entirety). Exemplary porphyrins are also described in Chen et al., Bromoporphyrins as Versatile Synthons for Modular Construction of Chiral Porphyrins: Cobalt-Catalyzed Highly Enantioselective and Diastereoselective Cyclopropanation (*J. Am. Chem. Soc.* 2004), which is incorporated herein by reference in its entirety.

In one embodiment, the cobalt porphyrin complex is a cobalt (II) porphyrin complex. In one particularly preferred embodiment, the cobalt porphyrin complex is a $D_2$-symmetric chiral porphyrin complex corresponding to the following structure

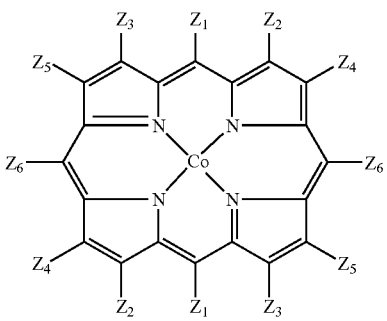

wherein each $Z_1, Z_2, Z_3, Z_4, Z_5$ and $Z_6$ are each independently selected from the group consisting of X, H, alkyl, substituted alkyls, arylalkyls, aryls and substituted aryls; and X is selected from the group consisting of halogen, triflouromethanesulfonate (OTf), haloaryl and haloalkyl. In a preferred embodiment, $Z_2, Z_3, Z_4$ and $Z_5$ are hydrogen, $Z_1$ is a substituted phenyl, and $Z_6$ is substituted phenyl, and $Z_1$ and $Z_6$ are different. In one particularly preferred embodiment, $Z_2, Z_3, Z_4$ and $Z_5$ are hydrogen, $Z_1$ is substituted phenyl, and $Z_6$ is substituted phenyl and $Z_1$ and $Z_6$ are different and the porphyrin is a chiral porphyrin. In one even further preferred embodiment, $Z_2, Z_3, Z_4$ and $Z_5$ are hydrogen, $Z_1$ is substituted phenyl, and $Z_6$ is substituted phenyl and $Z_1$ and $Z_6$ are different and the porphyrin has $D_2$-symmetry.

Exemplary cobalt (II) porphyrins include the following:

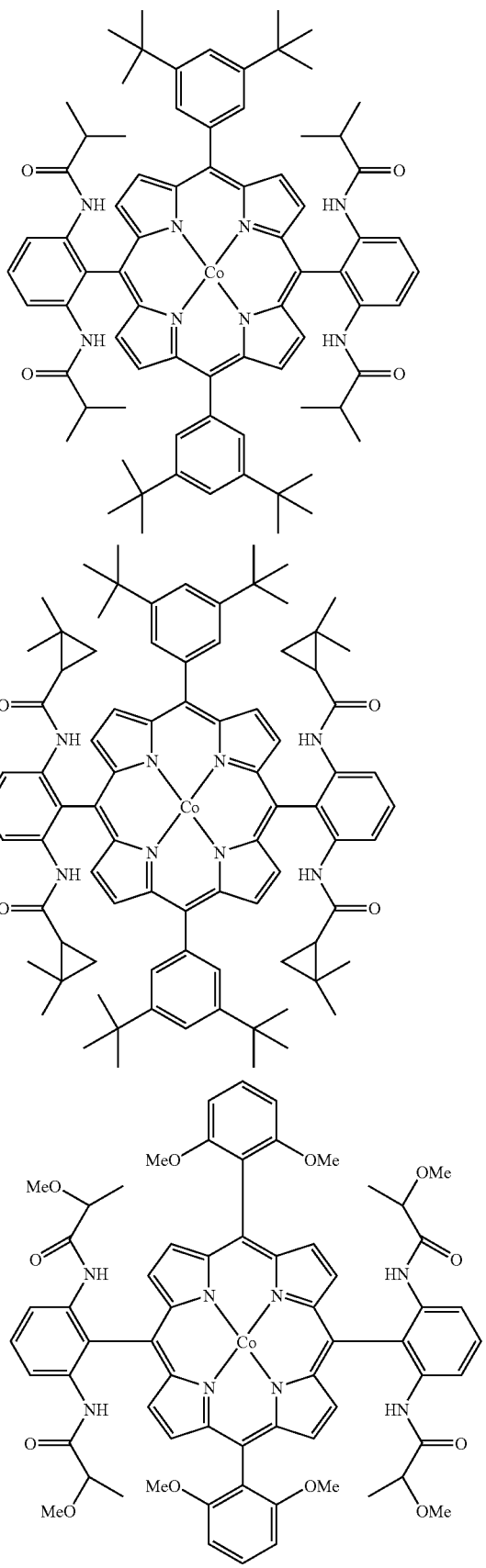

-continued

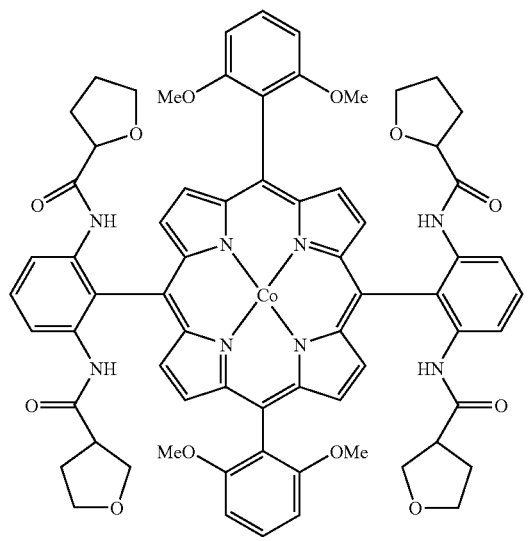

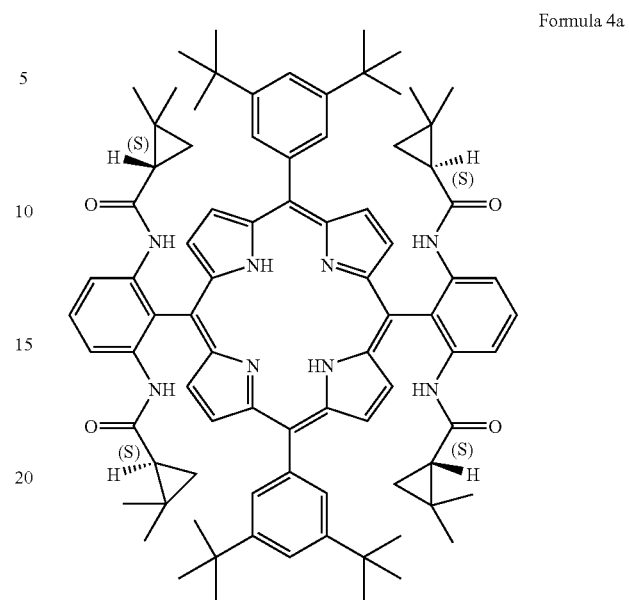

Formula 4a

[H₂(1)]

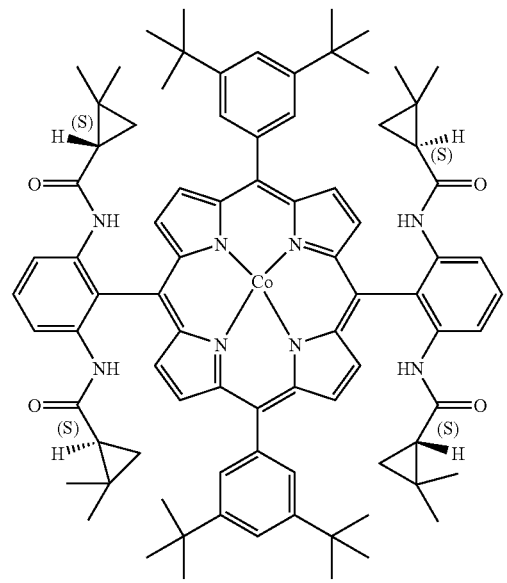

Formula 4b

[Co(1)]
Reaction Scheme B

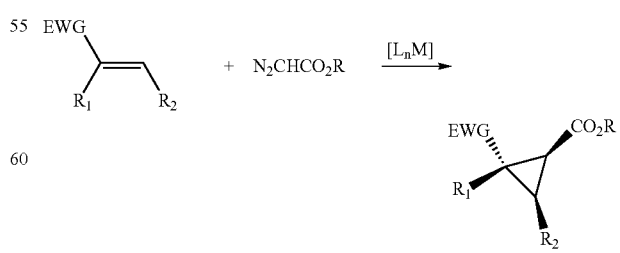

The cyclopropanation reaction could be carried out efficiently at room temperature in a one-pot fashion with olefins as limiting reagents and would not require the slow-addition of ester reagents. Additionally, the cyclopropanation reaction may be operated with relatively low catalyst loading, in a solvent such as toluene, chlorobenzene, tetrahydrofuran (THF), dichloromethane, or acetonitrile. The enantioselectivity and diastereoselectivity can be influenced, at least in part, by the selection of the solvent. In a preferred embodiment, the solvent is chlorobenzene, which was found to give the desired cyclopropane in the highest yield and with the best enantioselectivity as well as diastereoselectivity.

One aspect of the present invention is a general and efficient catalytic system for asymmetric cyclopropanation of electron-deficient olefins. Building on our previous work on Co-based asymmetric cyclopropanation, (Huang, L.; Chen, Y.; Gao, G.-Y.; Zhang, X. P. *J. Org. Chem.* 2003, 68, 8179; Chen, Y.; Fields, K. B.; Zhang, X. P. *J. Am. Chem. Soc.* 2004, 126, 14718; and Chen, Y.; Zhang, X. P. *J. Org. Chem.* 2007, 72, 5931), the Co(II) complex of the $D_2$-symmetric chiral porphyrin [Co(1)] (Formula 4b) was found to cyclopropanate a wide range of α,β-unsaturated carbonyl compounds and nitriles (Reaction Scheme B), forming the corresponding electrophilic cyclopropane derivatives in high yields and selectivities. Furthermore, the [Co(1)]-based catalytic process could be operated efficiently at room temperature in a one-pot fashion with olefins as limiting reagents and would not require the slow-addition of diazo reagents.

Previous studies on asymmetric cyclopropanation of styrene derivatives revealed that a [Co(1)]-based system seemed insensitive to substrate electronics. (Huang et al, *J. Org. Chem.* 2003, 68, 8179; Chen et al., *J. Am. Chem. Soc.* 2004, 126, 14718; and Chen Y., Zhang, X. P., *J. Org. Chem.* 2007, 72, 5931.) Even the extremely electron-deficient pentafluorostyrene could be cyclopropanated. (Chen Y., Zhang, X. P., *J. Org. Chem.* 2007, 72, 5931.) This result prompted us to evaluate the catalytic reactivity of [Co(1)] toward more challenging substrates such as electron-deficient non-styrene olefins (Table 1). Under the one-pot protocol where olefins are the limiting reagent, using 1 mol % [Co(1)] in the presence of 0.5 equivalents of DMAP could effectively cyclopropanate both acrylates and methacrylates with EDA or tert-butyl diazoacetate (t-BDA) at room temperature in toluene, forming the corresponding 1,2-cyclopropanediesters in good yields and high diastereo-as well as enantio-selectivities (Table 1, entries 1-5). Under the same conditions, acrylamide as well as its mono- and di-substituted derivatives were also suitable substrates, providing the corresponding 1,2-cyclopropaneamidoesters with good to high yields and excellent selectivities (Table 1, entries 6-10). The amido functional groups were well tolerated; no N—H insertion products were observed. Alkenes bearing carbonyl and cyano groups such as acrylketones and acrylonitriles were fully compatible with the catalytic system as well. In most of the cases, the resulting 1,2-cyclopropaneketoesters (Table 1, entries 11-15) and 1,2-cyclopropane cyanoesters (Table 1, entries 16-19) could be synthesized in high yields and high selectivities. As the best example, cyclopropanation of 1-octen-3-one with t-BDA resulted in the formation of the desired trans-1,2-cyclopropaneketoester in 94% yield, 98% de, and 96% ee (Table 1, entry 14). Diethyl maleate could also be successfully cyclopropanated to produce the 1,2,3-cyclopropanetriester solely as the α,α,β-isomer, albeit in a lower yield (Table 1, entry 20).

While most of the substrates gave high yields and selectivities, the yields of several reactions were still moderate (Table 1). To further improve the catalytic process without sacrificing its attractive practicality, several common solvents in addition to toluene were evaluated for the cyclopropanation of ethyl acrylate with t-BDA under the same conditions. Among the solvents tested (Table 2), chlorobenzene was found to be the best solvent, giving the desired cyclopropane in the highest yield and with the best enantioselectivity as well as diastereoselectivity. As a result, several lower-yielding reactions were repeated in chlorobenzene. Dramatic improvements in yield were obtained while maintaining high diastereo- and enantio-selectivities (Table 1, entries 1A-3A, 5A-7A, 10A, 15A, 18A, and 20A).

As demonstrated by the results reported in Table 1, [Co(1)] is an effective catalyst for asymmetric cyclopropanation of various electron-deficient olefins under mild conditions, forming synthetically valuable electrophilic cyclopropane derivatives in high yields and high stereoselectivities. Together with its high reactivity and selectivity toward styrene derivatives shown previously, [Co(1)] may be considered one of the most selective catalysts for asymmetric cyclopropanation of both electron-sufficient and electron-deficient olefins with diazoacetates. (Lebel et al., *Chem. Rev.* 2003, 103, 977; Davies H. M. L., Antoulinakis E., *Org. React.* 2001, 57, 1; Doyle M. P., Forbes D. C., *Chem. Rev.* 1998, 98, 911; Padwa A., Krumpe K. E., *Tetrahedron* 1992, 48, 5385-5453; Pietruszka J., *Chem. Rev.* 2003, 103, 1051; Wessjohann et al, *Chem. Rev.* 2003, 103, 1625; Donaldson W. A., *Tetrahedron* 2001, 57, 8589; Salaun J., *Chem. Rev.* 1989, 89, 1247; Fritschi et al, *Agnew. Chem., Int. Ed. Engl.* 1986, 25, 1005; Evans et al, *J. Am. Chem. Soc.* 1991, 113, 726; Lo et al, *J. Am. Chem. Soc.* 1998, 120, 10270; Maxwell et al, *Organometallics* 1992, 11, 645; Doyle et al, *J. Am. Chem. Soc.* 1993, 115, 9968; Davies et al., *J. Am. Chem. Soc.* 1996, 118, 6897; Nishiyama et al, *J. Am. Chem. Soc.* 1994, 116, 2223; Che et al, *J. Am. Chem. Soc.* 2001, 123, 4119.)

These results suggest that the catalytic intermediate of the current Co(II)-based system may have different reactivity characteristics from the previously reported either Cu(I)- or Rh(II)$_2$-based systems.

TABLE 1

Diastereoselective and Enantioselective Cyclopropanation of Electron-Deficient Olefins Catalyzed by [Co(1)].[a]

| entry | alkene | diazo | product | yield (%)[c] | t:c[d] | ee (%)[e] |
|---|---|---|---|---|---|---|
| 1 | CH$_2$=CHC(O)OEt | EDA | EtO-cyclopropane-OEt | 78 | 98:02 | 80[g] |
| 1A[b] | | | | 95 | 97:03 | 81[g] |
| 2 | CH$_2$=CHC(O)OEt | t-BDA | t-BuO-cyclopropane-OEt | 72 | 99:01 | 90 |
| 2A[b] | | | | 92 | 99:01 | 91 |
| 3 | CH$_2$=CHC(O)Ot-Bu | t-BDA | t-BuO-cyclopropane-Ot-Bu | 62 | 98:02 | 84 |
| 3A[b] | | | | 88 | 97:03 | 80 |
| 4 | CH$_2$=C(Me)C(O)OMe | EDA | EtO-cyclopropane(Me)-OMe | 73 | 95:05 | 61 |

TABLE 1-continued

Diastereoselective and Enantioselective Cyclopropanation of Electron-Deficient Olefins Catalyzed by [Co(1)].[a]

| entry | alkene | diazo | product | yield (%)[c] | t:c[d] | ee (%)[e] |
|---|---|---|---|---|---|---|
| 5<br>5A[b] | CH₂=C(Me)C(O)OMe | t-BDA | t-BuO-C(O)-cyclopropane-C(Me)-C(O)OMe | 62<br>90 | 93:07<br>93:07 | 84<br>83 |
| 6<br>6A[b] | CH₂=CHC(O)NH₂ | EDA | EtO-C(O)-cyclopropane-C(O)NH₂ | 51<br>81 | 99:01<br>99:01 | 88<br>90 |
| 7<br>7A[b] | CH₂=CHC(O)NH₂ | t-BDA | t-BuO-C(O)-cyclopropane-C(O)NH₂ | 66<br>77 | 99:01<br>99:01 | 97<br>97 |
| 8 | CH₂=CHC(O)NMe₂ | EDA | EtO-C(O)-cyclopropane-C(O)NMe₂ | 85 | 99:01 | 77 |
| 9 | CH₂=CHC(O)NMe₂ | t-BDA | t-BuO-C(O)-cyclopropane-C(O)NMe₂ | 86 | 99:01 | 96 |
| 10<br>10A[b] | CH₂=CHC(O)NHi-Pr | t-BDA | t-BuO-C(O)-cyclopropane-C(O)NHi-Pr | 44<br>96 | 99:01<br>99:01 | 97<br>96 |
| 11 | CH₂=CHC(O)Et | EDA | EtO-C(O)-cyclopropane-C(O)Et | 89 | 96:04 | 80 |
| 12 | CH₂=CHC(O)Et | t-BDA | t-BuO-C(O)-cyclopropane-C(O)Et | 81 | 99:01 | 94 |
| 13 | CH₂=CHC(O)n-Pe | EDA | EtO-C(O)-cyclopropane-C(O)n-Pe | 92 | 98:02 | 79 |
| 14 | CH₂=CHC(O)n-Pe | t-BDA | t-BuO-C(O)-cyclopropane-C(O)n-Pe | 94 | 99:01 | 96 |
| 15<br>15A[b] | CH₂=C(Me)C(O)Me | t-BDA | t-BuO-C(O)-cyclopropane-C(Me)-C(O)Me | 40<br>84 | 98:02<br>97:03 | 90<br>87 |

TABLE 1-continued

Diastereoselective and Enantioselective Cyclopropanation of Electron-Deficient Olefins Catalyzed by [Co(1)].[a]

| entry | alkene | diazo | product | yield (%)[c] | t:c[d] | ee (%)[e] |
|---|---|---|---|---|---|---|
| 16 |  | EDA | 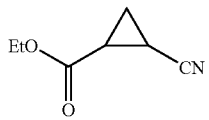 | 83 | 72:28 | 73 |
| 17 |  | t-BDA | 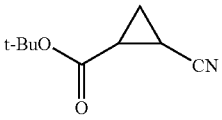 | 83 | 76:24 | 93 |
| 18<br>18A[b] |  | EDA | 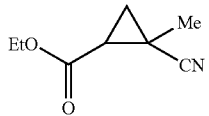 | 77<br>93 | 69:31<br>69:31 | 84<br>81 |
| 19 |  | t-BDA | 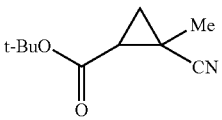 | 87 | 62:38 | 95 |
| 20<br>20A[b] |  | EDA | 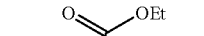 | 37<br>94 | >99:1[f]<br>>99:1[f] | —<br>— |

[a]Performed in toluene at RT for 20 h using 1 mol % [Co(1)] under $N_2$ with 1.0 equiv of alkene and 1.2 equiv of EDA or t-BDA in the presence of 0.5 equiv of DMAP. [alkene] = 0.25 M.
[b]Performed in chlorobenzene.
[c]Isolated yields.
[d]Determined by GC.
[e]Determined by GC or HPLC on chiral stationary phases.
[f]Only the □,□,□-isomer was observed.
[g](−)-[1R,2R] absolute configuration determined by optical rotation.

TABLE 2

Solvent Effect in [Co(1)]-Catalyzed Diastereoselective and Enantioselective Cyclopropanation of Electron-Deficient Olefins.[a]

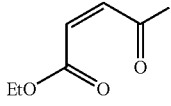

| entry | solvent | yield (%)[b] | trans:cis[c] | ee (%)[d] |
|---|---|---|---|---|
| 1 | $MeC_6H_5$ | 72 | 99:01 | 90 |
| 2 | $ClC_6H_5$ | 92 | 99:01 | 91 |
| 3 | THF | 29 | 88:12 | 76 |
| 4 | $CH_2Cl_2$ | 61 | 99:01 | 85 |
| 5 | $CH_3CN$ | 58 | 96:04 | 84 |

[a]Performed at room temperature for 20 h using 1 mol % [Co(1)] under $N_2$ with 1.0 equiv of alkene and 1.2 equiv of t-BDA in the presence of 0.5 equiv of DMAP. [alkene] = 0.25 M.
[b]Isolated yields.
[c]The trans:cis ratios were determined by GC.
[d]The ee of trans isomer was determined by chiral GC or chiral HPLC.

Example

All reactions were carried out under a nitrogen atmosphere in oven-dried glassware following standard Schlenk techniques. Proton and carbon nuclear magnetic resonance spectra ($^1$H NMR and $^{13}$C NMR) were recorded on a Varian Mercury 300 spectrometer and referenced with respect to internal TMS standard or residual solvent. HPLC measurements were carried out on a Hewlett-Packard HP1100 system with Whelk-O1 or Chiralcel OD-H column. GC-MS analysis was performed on a Hewlett-Packard G 1800B GCD system equipped with a CP-Chirasil-Dex CB or a Chiraldex G-TA column. Infrared spectra were obtained by using a Bomen B100 Series FT-IR spectrometer. HRMS data was obtained on an Agilent 1100 LC/MS ESI/TOF mass spectrometer with electrospray ionization. Optical rotation was performed on a Rudolph Research Analytical Autopol IV polarimeter (λ=365 nm) using a 0.8-mL cell with path length of 1-dm.

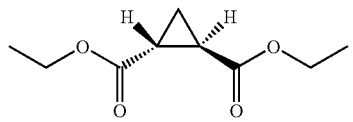

(−)-(1R,2R)-diethyl 1,2-cyclopropanedicarboxylate (Csuk R., von Scholz Y., *Tetrahedron* 1994, 50, 10431; Jeromin et al., *Ger. Offen.* 2006.) (Entry 1, Table 1) was synthesized from ethyl acrylate with EDA. trans-isomer: $[\alpha]^{27}_{365}=-452.1$ (c=0.42, CHCl$_3$). $^1$H NMR (300 MHz, CDCl$_3$): δ4.15 (q, J=7.2 Hz, 4H), 2.13-2.18 (m, 2H), 1.40-1.45 (m, 2H), 1.28 (t, J=7.2 Hz, 6H). $^{13}$C NMR (75 MHz, CDCl$_3$): δ171.8, 61.0, 22.3, 15.3, 14.1. IR (film, cm$^{-1}$): 1728 (C=O). HRMS (ESI): Calcd. for C$_9$H$_{15}$O$_4$ ([M+H]$^+$) m/z 187.0970, Found 187.0964. GC analysis: Chiraldex G-TA (Temp program: initial temp=50° C., 2.00° C./min, final temp=180° C., final time=10.00 min) trans-isomer: t$_{minor}$=30.46 min, t$_{major}$=30.74 min.

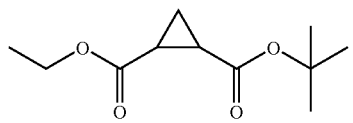

tert-Butyl ethyl 1,2-cyclopropanedicarboxylate (Bonavent et al., *Bull. Soc. Chim. Fr.* 1964, 10, 2462.) (Entry 2, Table 1) was synthesized from tert-butyl acrylate with EDA or from ethyl acrylate with t-BDA. trans-isomer: $^1$H NMR (300 MHz, CDCl$_3$): δ4.15 (q, J=7.2 Hz, 2H), 2.06-2.11 (m, 2H), 1.45 (s, 9H), 1.34-1.39 (m, 2H), 1.28 (t, J=7.2 Hz, 3H). $^{13}$C NMR (75 MHz, CDCl$_3$): δ172.0, 170.9, 81.2, 61.0, 28.0, 23.3, 22.0, 15.2, 14.1. IR (film, cm$^{-1}$): 1725 (C=O). HRMS (ESI): Calcd. for C$_{11}$H$_{22}$O$_4$N ([M+NH$_4$]$^+$) m/z 232.1549, Found 232.1545. GC analysis: CP-Chirasil-Dex CB (Temp program: initial temp=50° C., Rate$_1$: 10.00° C./min, max temp=100° C.; Rate$_2$: 2.00° C./min, max temp=140° C.; Rate$_3$: 10.00° C./min, max temp=200° C.; final time=0.00 min) trans-isomer: t$_{minor}$=21.18 min, t$_{major}$=21.36 min.

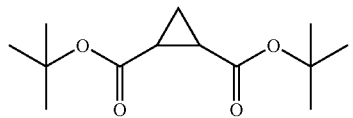

Di-tert-butyl 1,2-cyclopropanedicarboxylate (Artaud et al., *Acad. Sci., Ser. IIc: Chim.* 1976, 283, 503.) (Entry 3, Table 1) was synthesized from tert-butyl acrylate with t-BDA. trans-isomer: $^1$H NMR (300 MHz, CDCl$_3$): δ1.98-2.02 (m, 2H), 1.45 (s, 18H), 1.26-1.31 (m, 2H). $^{13}$C NMR (75 MHz, CDCl$_3$): δ171.1, 81.0, 28.0, 23.1, 15.2. IR (film, cm$^{-1}$): 1724 (C=O). HRMS (ESI): Calcd. for C$_{13}$H$_{26}$O$_4$N ([M+NH$_4$]$^+$) m/z 260.1862, Found 260.1856. GC analysis: CP-Chirasil-Dex CB (Temp program: initial temp=50° C., 10.00° C./min, final temp=200° C., final time=10.00 min) trans-isomer: t$_{minor}$=14.54 min, t$_{major}$=14.59 min.

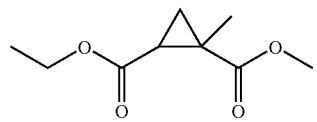

Ethyl methyl 1-methyl-1,2-cyclopropanedicarboxylate (Doyle et al., *J. Org. Chem.* 1982, 47, 4059.) (Entry 4, Table 1) was synthesized from methyl methacrylate with EDA. trans-isomer: $^1$H NMR (300 MHz, CDCl$_3$): δ4.17 (q, J=7.2 Hz, 2H), 3.70 (s, 3H), 2.30-2.36 (m, 1H), 1.55-1.59 (m, 1H), 1.40 (s, 3H), 1.31-1.34 (m, 1H), 1.28 (t, J=7.2 Hz, 3H). $^{13}$C NMR (75 MHz, CDCl$_3$): δ174.0 170.3, 60.9, 52.3, 27.9, 26.8, 20.9, 14.2, 13.0. IR (film, cm$^{-1}$): 1727 (C=O). HRMS (ESI): Calcd. for C$_9$H$_{18}$O$_4$N ([M+NH$_4$]$^+$) m/z 204.1236, Found 240.1229. GC analysis: CP-Chirasil-Dex CB (Temp program: initial temp=50° C., Rate$_1$: 3.00° C./min, max temp=100° C.; Rate$_2$: 2.00° C./min, max temp=130° C.; Rate$_3$: 10.00° C./min, max temp=200° C.; final time=5.00 min) trans-isomer: t$_{minor}$=25.36 min, t$_{major}$=25.47 min.

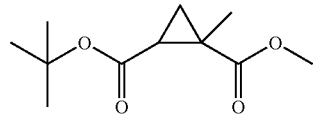

tert-Butyl methyl 1-methyl-1,2-cyclopropanedicarboxylate (Entry 5, Table 1) was synthesized from methyl methacrylate with t-BDA. trans-isomer: $^1$H NMR (300 MHz, CDCl$_3$): δ3.69 (s, 3H), 2.23-2.28 (m, 1H), 1.49-1.52 (m, 1H), 1.46 (s, 9H), 1.39 (s, 3H), 1.24-1.27 (m, 1H). $^{13}$C NMR (75 MHz, CDCl$_3$): δ174.2, 169.5, 81.1, 52.3, 28.3, 28.1, 26.5, 20.6, 12.9. IR (film, cm$^{-1}$): 1725 (C=O). HRMS (ESI): Calcd. for C$_{11}$H$_{22}$O$_4$N ([M+NH$_4$]$^+$) m/z 232.1549. Found 232.1541. HPLC analysis: Whelk-O1 (98% hexanes: 2% isopropanol, 1.0 mL/min) trans-isomer: t$_{major}$=7.01 min, t$_{minor}$=7.57 min.

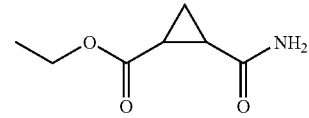

Ethyl 2-aminocarbonyl-cyclopropanecarboxylate (Kennewell et al., *J. Chem. Soc., Perkin Trans.* 1, 1982, 11, 2563.) (Entry 6, Table 1) was synthesized from acrylamide with EDA. trans-isomer: $^1$H NMR (300 MHz, CDCl$_3$): δ5.80 (br, 2H), 4.15 (q, J=7.2 Hz, 2H), 2.14-2.20 (m, 1H), 1.99-2.05 (m, 1H), 1.43-1.49 (m, 1H), 1.33-1.38 (m, 1H), 1.28 (t, J=7.2 Hz, 3H). $^{13}$C NMR (75 MHz, CDCl$_3$): δ172.5, 61.1, 23.4, 21.9, 15.0, 14.2. IR (film, cm$^{-1}$): 3202-3420 (NH), 1721 (C=O), 1669 (C=O), 1622 (C=O). HRMS (ESI): Calcd. for C$_7$H$_{12}$NO$_3$ ([M+H]$^+$) m/z 158.0817. Found 158.0813. GC analysis: CP-Chirasil-Dex CB (Temp program: initial temp=50° C., 10.00° C./min, final temp=200° C., final time=10.00 min) trans-isomer: t$_{major}$=17.36 min, t$_{minor}$=17.42 min.

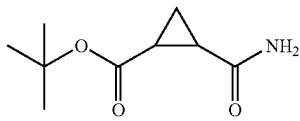

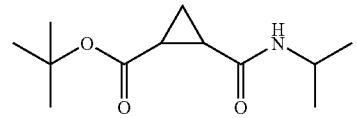

tert-Butyl 2-aminocarbonyl-cyclopropanecarboxylate (Entry 7, Table 1) was synthesized from acrylamide with t-BDA. trans-isomer: $^1$H NMR (300 MHz, CDCl$_3$): δ6.08 (br, 2H), 2.04-2.10 (m, 1H), 1.93-1.99 (m, 1H), 1.45 (s, 9H), 1.32-1.41 (m, 1H), 1.26-1.30 (m, 1H). $^{13}$C NMR (75 MHz, CDCl$_3$): δ173.2, 171.7, 81.2, 28.0, 23.1, 22.9, 14.8. IR (film, cm$^{-1}$): 3205-3421 (NH), 1717 (C=O), 1671 (C=O), 1623 (C=O). HRMS (ESI): Calcd. for C$_9$H$_{19}$N$_2$O$_3$ ([M+NH$_4$]$^+$) m/z 203.1396. Found 203.1389. GC analysis: CP-Chirasil-Dex CB (Temp program: initial temp=50° C., 10.00° C./min, final temp=200° C., final time=10.00 min) trans-isomer: t$_{minor}$=17.59 min, t$_{major}$=17.76 min.

tert-Butyl 2-isopropylaminocarbonyl-cyclopropanecarboxylate (Entry 10, Table 1) was synthesized from N-isopropylacylamide with t-BDA. trans-isomer: $^1$H NMR (300 MHz, CDCl$_3$): δ5.81 (br, 1H), 4.03-4.10 (m, 1H), 2.03-2.09 (m, 1H), 1.78-1.84 (m, 1H), 1.45 (s, 9H), 1.33-1.39 (m, 1H), 1.20-1.25 (m, 1H), 1.18 (d, J=4.2 Hz, 3H), 1.15 (d, J=4.5 Hz, 3H). $^{13}$C NMR (75 MHz, CDCl$_3$): δ172.0, 169.4, 80.9, 41.7, 28.0, 24.0, 22.7, 22.3, 14.5. IR (film, cm$^{-1}$): 3292 (NH), 1724 (C=O), 1643 (C=O). HRMS (ESI): Calcd. for C$_{12}$H$_{22}$NO$_3$ ([M+H]$^+$) m/z 228.1600. Found 228.1590. GC analysis: CP-Chirasil-Dex CB (Temp program: initial temp=50° C., 5.00° C./min, final temp=200° C., final time=10.00 min) trans-isomer: t$_{minor}$=28.15 min, t$_{major}$=28.26 min.

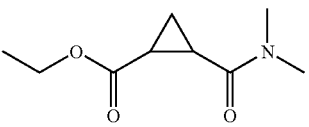

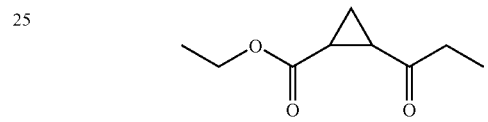

Ethyl 2-dimethylaminocarbonyl-cyclopropanecarboxylate (Entry 8, Table 1) was synthesized from N,N-dimethylacrylamide with EDA. trans-isomer: $^1$H NMR (300 MHz, CDCl$_3$): δ4.15 (q, J=7.2 Hz, 2H), 3.18 (s, 3H), 2.97 (s, 3H), 2.29-2.36 (m, 1H), 2.14-2.20 (m, 1H), 1.40-1.48 (m, 1H), 1.31-1.37 (m, 1H), 1.27 (t, J=7.2 Hz, 3H). $^{13}$C NMR (75 MHz, CDCl$_3$): δ172.8, 170.0, 60.7, 37.1, 35.7, 21.6, 20.8, 15.1, 14.0. IR (film, cm$^{-1}$): 3490 (NH), 1725 (C=O), 1642 (C=O). HRMS (ESI): Calcd. for C$_9$H$_{15}$NO$_3$Na ([M+Na]$^+$) m/z 208.0950. Found 208.0942. HPLC analysis: Chiralcel OD-H (90% hexanes: 10% isopropanol, 1.0 mL/min) trans-isomer: t$_{major}$=10.67 min, t$_{minor}$=11.78 min.

Ethyl 2-propionyl-cyclopropanecarboxylate (Hammerschmidt et al., *Annalen der Chemie,* 1977, 6, 1026.) (Entry 11, Table 1) was synthesized from ethyl vinyl ketone with EDA. trans-isomer: $^1$H NMR (300 MHz, CDCl$_3$): δ4.15 (q, J=7.2 Hz, 2H), 2.64 (q, J=7.2 Hz, 2H), 2.44-2.48 (m, 1H), 2.14-2.29 (m, 1H), 1.39-1.43 (m, 2H), 1.27 (t, J=7.2 Hz, 3H), 1.08 (t, J=7.2 Hz, 3H). $^{13}$C NMR (75 MHz, CDCl$_3$): δ208.1, 172.2, 61.0, 37.1, 28.7, 23.9, 17.0, 14.1, 7.6. IR (film, cm$^{-1}$): 1729 (C=O), 1707 (C=O). HRMS (ESI): Calcd. for C$_9$H$_{15}$O$_3$ ([M+H]$^+$) m/z 171.1021, Found 171.1016. GC analysis: CP-Chirasil-Dex CB (Temp program: initial temp=50° C., Rate$_1$: 3.00° C./min, max temp=100° C.; Rate$_2$: 2.00° C./min, max temp=130° C.; Rate$_3$: 10.00° C./min, max temp=200° C.; final time=5.00 min) trans-isomer: t$_{major}$=26.42 min, t$_{minor}$=26.84 min.

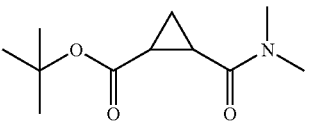

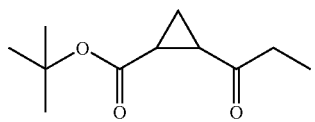

tert-Butyl 2-dimethylaminocarbonyl-cyclopropanecarboxylate (Entry 9, Table 1) was synthesized from N,N-dimethylacrylamide with t-BDA. trans-isomer: $^1$H NMR (300 MHz, CDCl$_3$): δ3.17 (s, 3H), 2.97 (s, 3H), 2.22-2.28 (m, 1H), 2.07-2.13 (m, 1H), 1.45 (s, 9H), 1.35-1.40 (m, 1H), 1.26-1.32 (m, 1H). $^{13}$C NMR (75 MHz, CDCl$_3$): δ172.1, 170.4, 80.9, 37.2, 35.8, 28.0, 22.7, 20.7, 15.0. IR (film, cm$^{-1}$): 3492 (NH), 1723 (C=O), 1645 (C=O). HRMS (ESI): Calcd. for C$_{11}$H$_{20}$NO$_3$ ([M+H]$^+$) m/z 214.1443. Found 214.1441. GC analysis: CP-Chirasil-Dex CB (Temp program: initial temp=50° C., 10.00° C./min, final temp=200° C., final time=10.00 min) trans-isomer: t$_{minor}$=16.05 min, t$_{major}$=16.12 min.

tert-Butyl 2-propionyl-cyclopropanecarboxylate (Entry 12, Table 1) was synthesized from ethyl vinyl ketone with t-BDA. trans-isomer: $^1$H NMR (300 MHz, CDCl$_3$): δ2.64 (q, J=7.2 Hz, 2H), 2.35-2.41 (m, 1H), 2.06-2.12 (m, 1H), 1.45 (s, 9H), 1.32-1.37 (m, 2H), 1.09 (t, J=7.2 Hz, 3H). $^{13}$C NMR (75 MHz, CDCl$_3$): δ208.3, 171.2, 81.1, 37.0, 28.5, 28.0, 25.0, 16.9, 7.6. IR (film, cm$^{-1}$): 1707 (C=O). HRMS (ESI): Calcd. for C$_{11}$H$_{22}$O$_3$N ([M+NH$_4$]$^+$) m/z 216.1600. Found 216.1592. GC analysis: CP-Chirasil-Dex CB (Temp program: initial temp=50° C., Rate$_1$: 3.00° C./min, max temp=100° C.; Rate$_2$: 2.00° C./min, max temp=130° C.; Rate$_3$: 10.00° C./min, max temp=200° C.; final time=5.00 min) trans-isomer: t$_{minor}$=30.11 min, t$_{major}$=30.40 min.

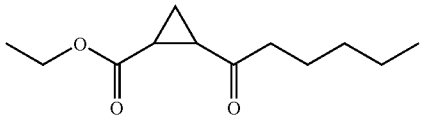

Ethyl 2-hexanoyl-cyclopropanecarboxylate (Ornstein et al., *J. Med. Chem.* 1998, 41, 346.) (Entry 13, Table 1) was synthesized from 1-octen-3-one with EDA. trans-isomer: $^1$H NMR (300 MHz, CDCl$_3$): δ4.13 (q, J=7.2 Hz, 2H), 2.59 (t, J=7.2 Hz, 2H), 2.41-2.47 (m, 1H), 2.12-2.18 (m, 1H), 1.56-1.66 (m, 2H), 1.39-1.43 (m, 2H), 1.26-1.33 (m, 4H), 1.27 (t, J=7.2 Hz, 3H), 0.89 (t, J=6.9 Hz, 3H). $^{13}$C NMR (75 MHz, CDCl$_3$): δ207.7, 172.1, 60.9, 43.9, 31.3, 28.8, 23.9, 23.4, 22.3, 17.0, 14.1, 13.8. IR (film, cm$^{-1}$): 1731 (C=O), 1706 (C=O). HRMS (ESI): Calcd. for C$_{12}$H$_{20}$O$_3$Na ([M+Na]$^+$) m/z 235.1310, Found 235.1305. GC analysis: CP-Chirasil-Dex CB (Temp program: initial temp=50° C., Rate$_1$: 5.00° C./min, max temp=100° C.; Rate$_2$: 0.90° C./min, max temp=140° C.; Rate$_3$: 10.00° C./min, max temp=200° C.; final time=5.00 min) trans-isomer: t$_{major}$=46.87 min, t$_{minor}$=47.39 min.

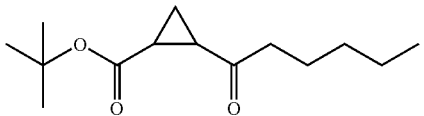

tert-Butyl 2-hexanoyl-cyclopropanecarboxylate (Entry 14, Table 1) was synthesized from 1-octen-3-one with t-BDA. trans-isomer: $^1$H NMR (300 MHz, CDCl$_3$): δ2.59 (t, J=7.5 Hz, 2H), 2.34-2.40 (m, 1H), 2.04-2.10 (m, 1H), 1.56-1.66 (m, 2H), 1.45 (s, 9H), 1.25-1.35 (m, 6H), 0.90 (t, J=6.9 Hz, 3H). $^{13}$C NMR (75 MHz, CDCl$_3$): δ208.0, 171.2, 81.0, 43.8, 31.3, 28.6, 28.0, 25.0, 23.4, 22.4, 16.8, 13.8. IR (film, cm$^{-1}$): 1707 (C=O). HRMS (ESI): Calcd. for C$_{14}$H$_{24}$O$_3$Na ([M+Na]$^+$) m/z 263.1623. Found 263.1616. GC analysis: CP-Chirasil-Dex CB (Temp program: initial temp=50° C., Rate$_1$: 5.00° C./min, max temp=100° C.; Rate$_2$: 2.00° C./min, max temp=150° C.; Rate$_3$: 10.00° C./min, max temp=200° C.; final time=5.00 min) trans-isomer: t$_{minor}$=37.71 min, t$_{minor}$=37.91 min.

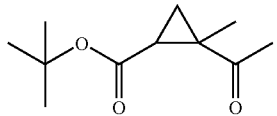

tert-Butyl 2-acetyl-2-methyl-cyclopropanecarboxylate (Entry 15, Table 1) was synthesized from 3-methyl-3-buten-2-one with t-BDA. trans-isomer: $^1$H NMR (300 MHz, CDCl$_3$): δ2.20-2.25 (m, 1H), 2.21 (s, 3H), 1.48 (s, 3H), 1.42-1.50 (m, 1H), 1.46 (s, 9H), 1.24-1.27 (m, 1H). $^{13}$C NMR (75 MHz, CDCl$_3$): δ207.5, 169.5, 81.1, 33.6, 30.0, 28.1, 26.8, 21.7, 13.6. IR (film, cm$^{-1}$): 1728 (C=O). HRMS (ESI): Calcd. for C$_{11}$H$_{22}$O$_3$N ([M+NH$_4$]$^+$) m/z 216.1600. Found 216.1588. GC analysis: CP-Chirasil-Dex CB (Temp program: initial temp=50° C., 4.00° C./min, final temp=200° C., final time=10.00 min) trans-isomer: t$_{minor}$=22.80 min, t$_{major}$=22.91 min.

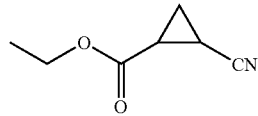

Ethyl 2-cyanocyclopropanecarboxylate (Ashton et al., *J. Med. Chem.* 1988, 31, 2304.) (Entry 16, Table 1) was synthesized from acrylonitrile with EDA. trans-isomer: $^1$H NMR (300 MHz, CDCl$_3$): δ4.19 (q, J=7.2 Hz, 2H), 2.23-2.30 (m, 1H), 1.91-1.98 (m, 1H), 1.48-1.56 (m, 2H), 1.30 (t, J=7.2 Hz, 3H). $^{13}$C NMR (75 MHz, CDCl$_3$): δ170.1, 119.2, 61.7, 21.0, 14.4, 14.1, 5.6. IR (film, cm$^{-1}$): 2245 (CN), 1730 (C=O). HRMS (ESI): Calcd. for C$_7$H$_{13}$N$_2$O$_2$ ([M+NH$_4$]$^+$) m/z 157.0977. Found 157.0972. cis-isomer: $^1$H NMR (300 MHz, CDCl$_3$): δ4.26 (q, J=7.2 Hz, 2H), 2.09-2.16 (m, 1H), 1.81-1.89 (m, 1H), 1.66-1.72 (m, 1H), 1.38-1.46 (m, 1H), 1.32 (t, J=7.2 Hz, 3H). $^{13}$C NMR (75 MHz, CDCl$_3$): δ168.8, 100.1, 61.7, 20.0, 14.1, 13.2, 5.6. IR (film, cm$^{-1}$): 2245 (CN), 1730 (C=O). HRMS (ESI): Calcd. for C$_7$H$_{13}$N$_2$O$_2$ ([M+NH$_4$]$^+$) m/z 157.0977. Found 157.0972. GC analysis: G-TA (Temp program: initial temp=50° C., 10.00° C./min, final temp=180° C., final time=10.00 min) trans-isomer: t$_{major}$=11.69 min, t$_{minor}$=11.83 min; cis-isomer: t$_{minor}$=14.74 min, t$_{major}$=15.15 min.

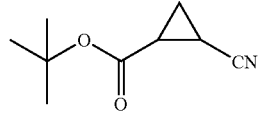

tert-Butyl 2-cyanocyclopropanecarboxylate (Jonczyk A., Makosza M., *Synthesis* 1976, 6, 387.) (Entry 17, Table 1) was synthesized from acrylonitrile with t-BDA. trans-isomer: $^1$H NMR (300 MHz, CDCl$_3$): δ2.14-2.21 (m, 1H), 1.83-1.90 (m, 1H), 1.38-1.50 (m, 2H), 1.46 (s, 9H). $^{13}$C NMR (75 MHz, CDCl$_3$): δ169.1, 119.5, 82.4, 27.9, 22.0, 14.3, 5.3. IR (film, cm$^{-1}$): 2240 (CN), 1718 (C=O). HRMS (ESI): Calcd. for C$_9$H$_{17}$N$_2$O$_2$ ([M+NH$_4$]$^+$) m/z 185.1290. Found 185.1286. cis-isomer: $^1$H NMR (300 MHz, CDCl$_3$): δ1.98-2.05 (m, 1H), 1.72-1.81 (m, 1H), 1.58-1.66 (m, 1H), 1.51 (s, 9H), 1.31-1.39 (m, 1H). $^{13}$C NMR (75 MHz, CDCl$_3$): δ167.7, 117.8, 82.5, 27.9, 20.9, 12.9, 5.3. IR (film, cm$^{-1}$): 2241 (CN), 1725 (C=O). HRMS (ESI): Calcd. for C$_9$H$_{17}$N$_2$O$_2$ ([M+NH$_4$]$^+$) m/z 185.1290, Found 185.1289. GC analysis: CP-Chirasil-Dex CB (Temp program: initial temp=50° C., 10.00° C./min, final temp=200° C., final time=10.00 min) trans-isomer: t$_{major}$=12.92 min, t$_{minor}$=13.06 min; cis-isomer: t$_{minor}$=13.81 min, t$_{major}$=13.90 min.

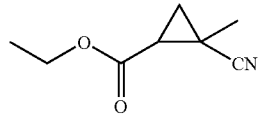

Ethyl 2-cyano-2-methylcyclopropanecarboxylate (Doyle M. P., Davidson J. G., *J. Org. Chem.* 1980, 45, 1538.) (Entry 18, Table 1) was synthesized from methacrylonitrile with EDA. trans-isomer: $^1$H NMR (300 MHz, CDCl$_3$): δ4.20 (q, J=7.2 Hz, 2H), 2.29-2.34 (m, 1H), 1.58-1.63 (m, 1H), 1.50 (s, 3H), 1.40-1.42 (m, 1H), 1.30 (t, J=7.2 Hz, 3H). $^{13}$C NMR (75 MHz, CDCl$_3$): δ168.6, 122.4, 61.5, 26.0, 19.7, 14.7, 14.1, 13.8. IR (film, cm$^{-1}$): 2243 (CN), 1732 (C=O). cis-isomer: $^1$H NMR (300 MHz, CDCl$_3$): δ4.24 (q, J=7.2 Hz, 2H), 1.81-1.92 (m, 2H), 1.50 (s, 3H), 1.31 (t, J=7.2 Hz, 3H), 1.20-1.25 (m, 1H). $^{13}$C NMR (75 MHz, CDCl$_3$): δ168.8, 120.0, 61.7, 27.9, 21.8, 20.9, 14.2, 12.9. IR (film, cm$^{-1}$): 2243 (CN), 1731 (C=O). HRMS (ESI): Calcd. for C$_8$H$_{15}$N$_2$O$_2$ ([M+NH$_4$]$^+$) m/z 171.1134. Found 171.1128. GC analysis: CP-Chirasil-Dex CB (Temp program: initial temp=50° C., 10.00° C./min, final temp=200° C., final time=10.00 min) trans-isomer: t$_{minor}$=11.76 min, t$_{major}$=11.87 min; cis-isomer: t$_{minor}$=12.32 min, t$_{major}$=12.59 min.

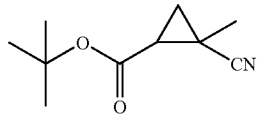

tert-Butyl 2-cyano-2-methylcyclopropanecarboxylate (Jonczyk A., Makosza M., *Synthesis* 1976, 6, 387.) (Entry 19, Table 1) was synthesized from methacrylonitrile with t-BDA. trans-isomer: $^1$H NMR (300 MHz, CDCl$_3$): δ2.21-2.26 (m, 1H), 1.52-1.58 (m, 1H), 1.50 (s, 3H), 1.47 (s, 9H), 1.33-1.37 (m, 1H). $^{13}$C NMR (75 MHz, CDCl$_3$): δ 167.6, 122.7, 82.2, 28.0, 27.2, 19.3, 14.6, 12.2. IR (film, cm$^{-1}$): 2239 (CN), 1726 (C=O). HRMS (ESI): Calcd. for C$_{10}$H$_{19}$N$_2$O$_2$ ([M+NH$_4$]$^+$) m/z 199.1447, Found 199.1438. cis-isomer: $^1$H NMR (300 MHz, CDCl$_3$): δ1.73-1.81 (m, 2H), 1.50 (s, 9H), 1.47 (s, 3H), 1.13-1.17 (m, 1H). $^{13}$C NMR (75 MHz, CDCl$_3$): δ167.8, 120.2, 82.4, 28.9, 28.0, 21.8, 20.7, 13.4. IR (film, cm$^{-1}$): 2243 (CN), 1726 (C=O). HRMS (ESI): Calcd. for C$_{10}$H$_{16}$NO$_2$ ([M+H]$^+$) m/z 182.1181. Found 182.1172. GC analysis: CP-Chirasil-Dex CB (Temp program: initial temp=50° C., 10.00° C./min, final temp=200° C., final time=10.00 min) trans-isomer: t$_{minor}$=12.63 min, t$_{major}$=12.70 min; cis-isomer: t$_{minor}$=12.83 min, t$_{major}$=12.92 min.

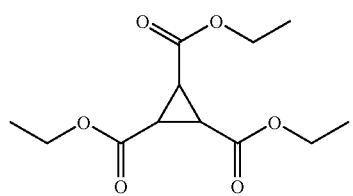

Tiethyl trans-1,2,3-cyclopanetricarboxylate (Kozhushkov et al., *Synthesis* 2003, 6, 956.) (Entry 20, Table 1) was synthesized from diethyl maleate with EDA. $^1$H NMR (300 MHz, CDCl$_3$): δ4.18 (q, J=7.2 Hz, 2H), 4.17 (q, J=7.2 Hz, 4H), 2.77 (t, J=5.7 Hz, 1H), 2.54 (d, J=5.1 Hz, 2H), 1.29 (t, J=7.2 Hz, 3H), 1.27 (t, J=7.2 Hz, 6H). $^{13}$C NMR (75 MHz, CDCl$_3$): δ170.1, 167.5, 61.6, 61.5, 28.4, 25.6, 14.0. IR (film, cm$^{-1}$): 1731 (C=O). HRMS (ESI): Calcd. for C$_{12}$H$_{22}$O$_6$N ([M+NH$_4$]$^+$) m/z 276.1447. Found 276.1435.

The foregoing non-limiting examples are provided to illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

What is claimed is:

1. An asymmetric cyclopropanation process, the process comprising cyclopropanating an electron-deficient olefin with a cobalt(II) complex of a D$_2$-symmetric chiral cobalt (II) porphyrin complex and a carbene wherein at least one of the olefinic carbon atoms of the electron-deficient olefin is substituted by an electron withdrawing group selected from the group consisting of hydroxy, alkoxy, mercapto, halo, carbonyl, sulfonyl, nitrile, quaternary amine, nitro, trihalomethyl, imine, amidine, oxime, thioketone, thioester, and thioamide.

2. A process for asymmetric cyclopropanation of an olefin substrate wherein at least one of the olefinic carbon atoms of the olefin substrate is substituted by an electron withdrawing group, the process comprising treating the olefin substrate with a diazo ester reagent in the presence of a chiral porphyrin catalyst.

3. The process of claim 2 wherein the olefin substrate corresponds to Formula 1

wherein EWG is an electron withdrawing group, R$_1$ is hydrogen, hydrocarbyl, substituted hydrocarbyl, or heterocyclo and R$_2$ and R$_3$ are independently hydrogen, hydrocarbyl, substituted hydrocarbyl, heterocyclo, or an electron withdrawing group.

4. The process of claim 2 wherein the olefin substrate corresponds to Formula 2

wherein EWG is an electron withdrawing group, and R$_2$ and R$_3$ are independently hydrogen, hydrocarbyl, substituted hydrocarbyl, heterocyclo, or an electron withdrawing group.

5. The process of claim 2 wherein the olefin substrate corresponds to Formula 2-trans or Formula 2-cis:

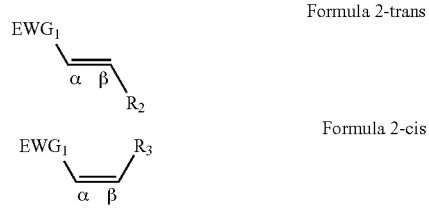

wherein EWG$_1$ is an electron withdrawing group, R$_2$ and R$_3$ are independently hydrogen, hydrocarbyl, substituted hydrocarbyl, heterocyclo, or EWG$_2$, EWG$_2$ is an electron withdrawing group, and EWG$_1$ and EWG$_2$ are the same or are different.

6. The process claim 2 wherein the olefin substrate corresponds to Formula 3:

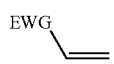

Formula 3 wherein EWG is an electron withdrawing group.

7. The process of claim 2 wherein the electron withdrawing group is an electron withdrawing group selected from the group consisting of hydroxy, alkoxy, mercapto, halo, carbonyl, sulfonyl, nitrile, quaternary amine, nitro, trihalomethyl, imine, amidine, oxime, thioketone, thioester, and thioamide.

8. The process of claim 3 wherein the electron withdrawing group is an electron withdrawing group selected from the group consisting of halo, aldehyde, ketone, ester, carboxylic acid, amide, acid halide, trifluoromethyl, nitrile, sulfonic acid, and nitro.

9. The process of claim 3 wherein EWG is a carbonyl moiety.

10. The process of claim 3 wherein EWG is a nitrile.

11. The process of claim 7 wherein the electron withdrawing group is selected from the group consisting of amide, ester, ketone, and aldehyde.

12. The process of claim 7 wherein the electron withdrawing group is selected from the group consisting of imine, amidine, oxime, thioketone, thioester, and thioamide.

13. The process of claim 4 wherein EWG is an electron withdrawing group selected from the group consisting of hydroxy, alkoxy, mercapto, halo, carbonyl, sulfonyl, nitrile, quaternary amine, nitro, trihalomethyl, imine, amidine, oxime, thioketone, thioester, and thioamide.

14. The process of claim 4 wherein EWG is a carbonyl moiety.

15. The process of claim 4 wherein EWG is a nitrile.

16. The process of claim 13 wherein EWG is selected from the group consisting of amide, ester, ketone, and aldehyde.

17. The process of claim 13 wherein EWG is selected from the group consisting of imine, amidine, oxime, thioketone, thioester, and thioamide.

18. The process of claim 5 wherein $EWG_1$ and $EWG_2$ are independently selected from the group consisting of hydroxy, alkoxy, mercapto, halo, carbonyl, sulfonyl, nitrile, quaternary amine, nitro, trihalomethyl, imine, amidine, oxime, thioketone, thioester, and thioamide.

19. The process of claim 5 wherein $EWG_1$ is a carbonyl moiety.

20. The process of claim 5 wherein $EWG_1$ is a nitrile.

21. The process of claim 5 wherein $EWG_2$ is a carbonyl moiety.

22. The process of claim 5 wherein $EWG_2$ is a nitrile.

23. The process of claim 18 wherein $EWG_1$ and $EWG_2$ are independently selected from the group consisting of amide, ester, ketone and aldehyde.

24. The process of claim 18 wherein $EWG_1$ and $EWG_2$ are independently selected from the group consisting of an imine, amidine, oxime, thioketone, thioester and thioamide.

25. The process of claim 6 wherein EWG is an electron withdrawing group selected from the group consisting of hydroxy, alkoxy, mercapto, halo, carbonyl, sulfonyl, nitrile, quaternary amine, nitro, trihalomethyl, imine, amidine, oxime, thioketone, thioester, and thioamide.

26. The process of claim 6 wherein EWG is a nitrile.

27. The process of claim 6 wherein EWG is a carbonyl moiety.

28. The process of claim 25 wherein EWG is selected from the group consisting of amide, ester, ketone and aldehyde.

29. The process of claim 25 wherein EWG is selected from the group consisting of an imine, amidine, oxime, thioketone, thioester, and thioamide.

30. The process of claim 2 wherein the cobalt porphyrin complex is selected from the group of cobalt porphyrin complex consisting of:

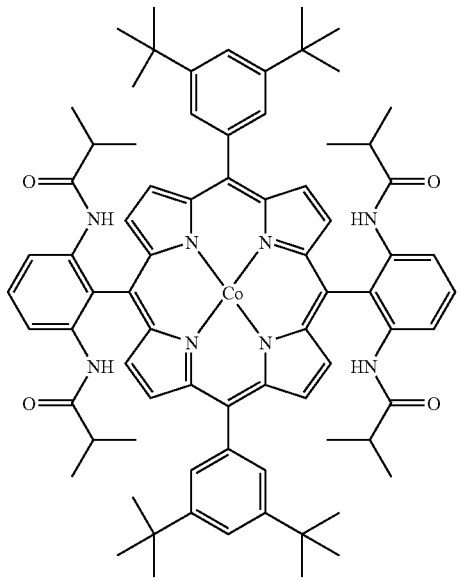

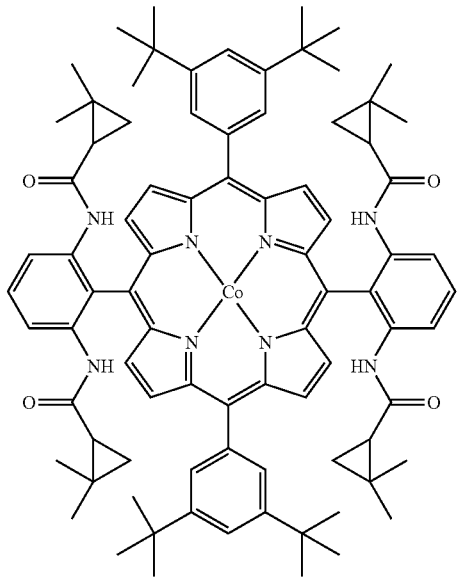

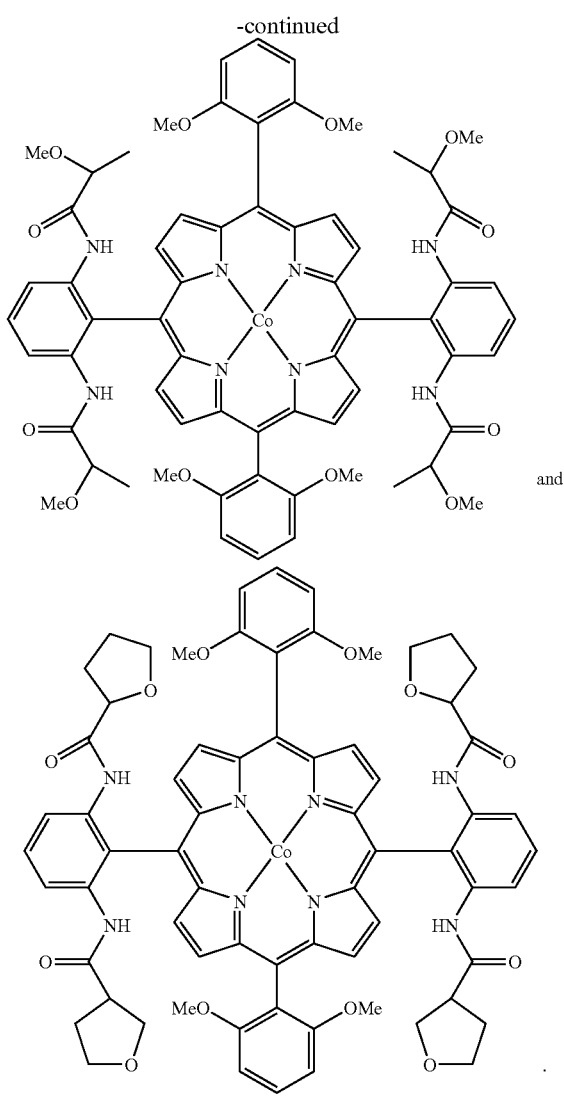
and

31. The process of claim 2 wherein the cobalt porphyrin complex is a $D_2$-symmetric chiral cobalt (II) porphyrin complex.

32. The process of claim 3 wherein the cobalt porphyrin complex is a $D_2$-symmetric chiral cobalt (II) porphyrin complex.

33. The process of claim 4 wherein the cobalt porphyrin complex is a $D_2$-symmetric chiral cobalt (II) porphyrin complex.

34. The process of claim 5 wherein the cobalt porphyrin complex is a $D_2$-symmetric chiral cobalt (II) porphyrin complex.

35. The process of claim 6 wherein the cobalt porphyrin complex is a $D_2$-symmetric chiral cobalt (II) porphyrin complex.

36. The process of claim 1 wherein the carbene is derived from a diazo reagent having the formula $N_2CHC(O)OR_{10}$ and $R_{10}$ is hydrocarbyl, substituted hydrocarbyl or heterocyclo.

37. The process of claim 36 wherein $R_{10}$ is alkyl, aryl or alkaryl.

38. The process of claim 1 wherein the electron-deficient olefin is an α,β-unsaturated carbonyl compound or an α,β-unsaturated nitrile compound.

39. The process of claim 1 wherein the electron-deficient olefin is an α,β-unsaturated carbonyl compound or an α,β-unsaturated nitrile compound, the carbene is derived from a diazo reagent having the formula $N_2CHC(O)OR_{10}$, and $R_{10}$ is alkyl, aryl or alkaryl.

40. The process of claim 2 wherein the diazo ester reagent has the formula $N_2CHC(O)OR_{10}$ and $R_{10}$ is alkyl, aryl or alkaryl.

41. The process of claim 3 wherein the diazo ester reagent has the formula $N_2CHC(O)OR_{10}$ and $R_{10}$ is alkyl, aryl or alkaryl.

42. The process of claim 4 wherein the diazo ester reagent has the formula $N_2CHC(O)OR_{10}$ and $R_{10}$ is alkyl, aryl or alkaryl.

43. The process of claim 5 wherein the diazo ester reagent has the formula $N_2CHC(O)OR_{10}$ and $R_{10}$ is alkyl, aryl or alkaryl.

44. The process of claim 6 wherein the diazo ester reagent has the formula $N_2CHC(O)OR_{10}$ and $R_{10}$ is alkyl, aryl or alkaryl.

45. A process for asymmetric cyclopropanation of an olefin substrate wherein at least one of the olefinic carbon atoms of the olefin substrate is substituted by an electron withdrawing group, the process comprising treating the olefin substrate with a diazo ester reagent in the presence of a chiral porphyrin catalyst, wherein the olefin substrate corresponds to Formula 1, Formula 1

the diazo ester reagent has the formula $N_2CHC(O)OR_{10}$,

EWG is an electron withdrawing group, $R_1$ is hydrogen, hydrocarbyl, substituted hydrocarbyl, or heterocyclo, $R_2$ and $R_3$ are independently hydrogen, hydrocarbyl, substituted hydrocarbyl, heterocyclo, or an electron withdrawing group, and $R_{10}$ is hydrocarbyl, substituted hydrocarbyl or heterocyclo.

46. The process of claim 45 wherein EWG is an electron withdrawing group selected from the group consisting of halo, aldehyde, ketone, ester, carboxylic acid, amide, acid halide, trifluoromethyl, nitrile, sulfonic acid, and nitro.

47. The process of claim 45 wherein EWG is a carbonyl moiety or a nitrile.

48. The process of claim 45 wherein the cobalt porphyrin complex is selected from the group of cobalt porphyrin complex consisting of:

-continued
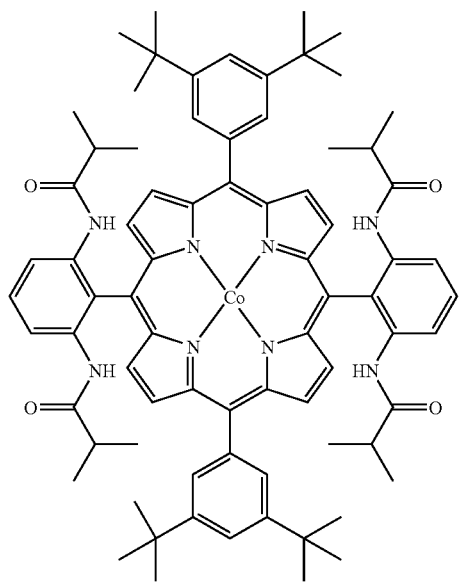
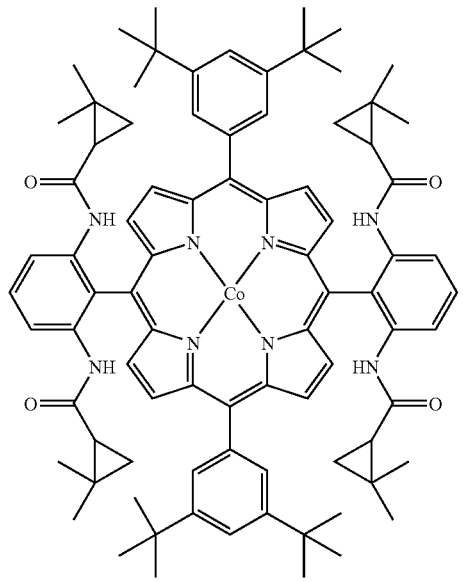
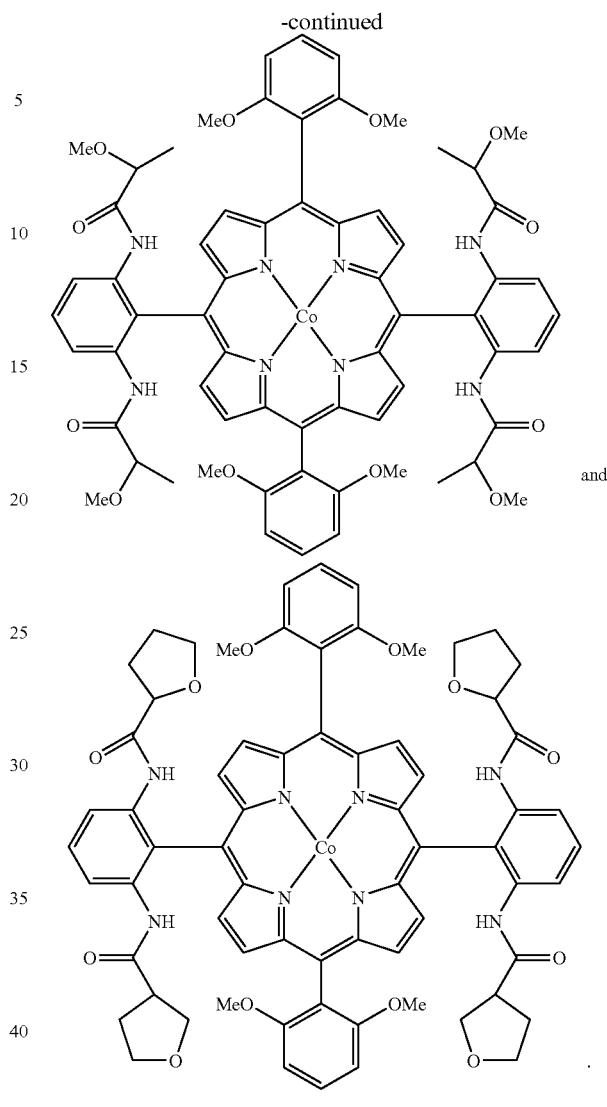
49. The process of claim 45 wherein the cobalt porphyrin complex is a $D_2$-symmetric chiral cobalt (II) porphyrin complex.
* * * * *